United States Patent [19]

Nishio

[11] 4,405,429
[45] Sep. 20, 1983

[54] OXYGEN DETECTOR
[75] Inventor: Hisaharu Nishio, Tokai, Japan
[73] Assignee: N G K Spark Plug Co., Ltd., Nagoya, Japan
[21] Appl. No.: 233,477
[22] Filed: Feb. 11, 1981
[30] Foreign Application Priority Data Feb. 15, 1980 [JP] Japan .............................. 55-18936[U]

[51] Int. Cl.³ ............................................ G01N 27/46
[52] U.S. Cl. .................................. 204/421; 174/74 R
[58] Field of Search ........................... 204/1 S, 195 S; 174/74 R

[56] References Cited
U.S. PATENT DOCUMENTS

| 4,088,555 | 5/1978 | Kita et al. | 204/195 S |
| 4,127,464 | 11/1978 | Ichikawa et al. | 204/195 S |
| 4,141,813 | 2/1979 | Kita et al. | 204/195 S |
| 4,210,510 | 7/1980 | Grimes | 204/195 S |
| 4,218,297 | 8/1980 | Henault et al. | 204/195 S |

FOREIGN PATENT DOCUMENTS 52-27696 3/1977 Japan .............................. 204/195 S
53-144392 11/1978 Japan .

OTHER PUBLICATIONS

United States Defensive Publication T979,002, Feb. 6, 1979.

*Primary Examiner*—T. Tung
*Attorney, Agent, or Firm*—Fleit, Jacobson & Cohn

[57] ABSTRACT

An oxygen detector for detecting concentration of oxygen in exhaust gas delivered from various kinds of combustion apparatus inclusive of an internal combustion engine or the like and comprising a resilient portion operative to apply a tensile or compressive force to a coil-shaped terminal of a center conductor threadedly engaged with the threaded open end of an inner electrode layer of an oxygen detection element.

13 Claims, 1 Drawing Figure

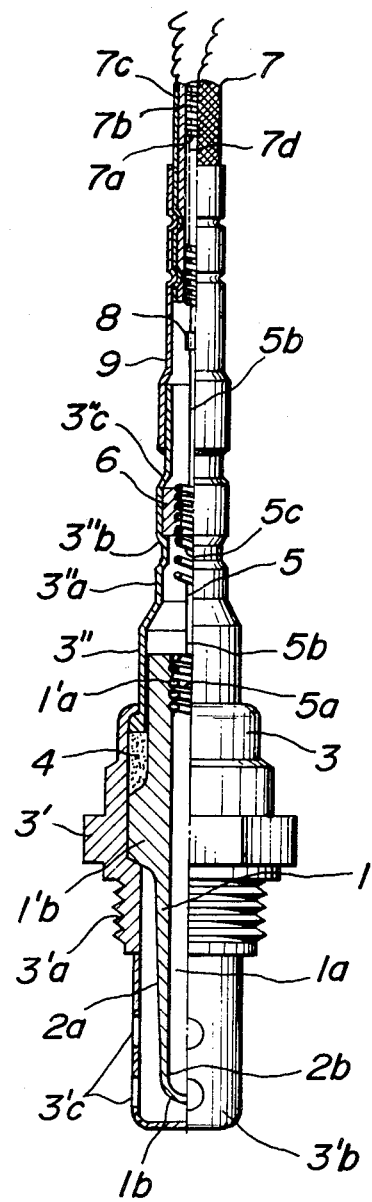

OXYGEN DETECTOR

BACKGROUND OF THE INVENTION

1. Field of the Invention

This invention relates to an oxygen detector for detecting concentration of oxygen in exhaust gas delivered from various kinds of combustion apparatus inclusive of an internal combustion engine or the like.

2. Description of the Prior Art

An oxygen detector for detecting concentration of oxygen in exhaust gas delivered from various kinds of combustion apparatus inclusive of an internal combustion engine or the like and including an oxygen detection element composed of a solid electrolyte has heretofore been widely used.

In such kind of oxygen detector, provision is made of a tubular oxygen detection element formed of zirconia or the like and closed at one end thereof. The oxygen detection element is provided at its outer and inner peripheral walls with outer and inner electrode layers, respectively, each extending upwardly from the closed end of the oxygen detection element and formed of platinum deposited thereon by printing or the like. The oxygen detection element must be sealed and electrically conductive with a metal casing which is provided with small holes through which flows exhaust gas which makes contact with the outer electrode layer. Meanwhile, outside air must be introduced through the inner electrode into the closed end of the oxygen detection element and at the same time a lead wire connected to the inner electrode layer must be led to the outside. In this case, the outer electrode layer can easily be sealed with the metal casing, but means for allowing the outside air to introduce into the inner electrode layer of the oxygen detection element and at the same time allowing the lead wire connected to the inner electrode layer to lead out upwardly involves various drawbacks.

In order to eliminate such drawbacks, an attempt has been made that the inner electrode layer is provided at its open end with a threaded portion with which a coil-shaped terminal having an outer diameter which is slightly larger than the inner diameter of the tapped portion is threadedly engaged under pressure and that a lead wire extending upwardly from the coil-shaped terminal is connected to one of output delivery conductors. Such attempt is satisfactory under a normal condition, but has the drawback that there is a risk of the electrical conduction between the oxygen detection element and the inner electrode layer being deteriorated under a high temperature condition.

That is, the above mentioned coil-shaped terminal is preferably formed of a spring material consisting of stainless steel such as SUS631J1 having an excellent heat resistant property. The inner diameter of the open end and the diameter of the thread provided therein of the oxygen detection element are limited for the sake of construction and the coil-shaped terminal threadedly engaged under pressure with the threaded open end of the oxygen detection element must be formed of a wire having a small diameter for the sake of the threaded engagement. Under such circumstances, if the oxygen detector is used at a high temperature for a long time, the coil-shaped terminal becomes softened to reduce its tensile force when it is threadedly engaged with the threaded open end of the oxygen detection element, thereby deteriorating the electrical conduction between the oxygen detection element and the inner electrode layer. For example, if a coil-shaped terminal formed of a spring material consisting of SUS631J1 and having a diameter of 0.6 mm was used at 300° C., its tensile force was not reduced, but if it was continuously used at 400° C. for 100 hours, its tensile force was reduced.

SUMMARY OF THE INVENTION

An object of the invention, therefore, is to provide an oxygen detector which can eliminate the above mentioned drawbacks which have been encountered with the prior art techniques and which has a highly excellent electrical stability.

A feature of the invention is a provision of an oxygen detector comprising a tubular oxygen detection element closed at one end and including outer and inner electrode layers extending upwardly from the closed end, a metal casing sealed and electrically conductive with the oxygen detection element, a center conductor including a coil-shaped terminal threadedly engaged with the threaded open end of said inner electrode layer and communicating the inner electrode layer with the outside air and an output delivering electric wire connected to the ends of said center conductor and said metal casing and having a communication hole communicated through said coil-shaped terminal with the inner electrode layer of the oxygen detection element, characterized by comprising a resilient portion operative to apply a tensile or compressive force to said coil-shaped terminal of said center electrode.

Further objects and features of the invention will be fully understood from the following detailed description with reference to the accompanying drawing, wherein:

BRIEF DESCRIPTION OF THE DRAWING

A single FIGURE is a front elevational view of one embodiment of an oxygen detector according to the invention, partly shown in section.

DETAILED DESCRIPTION OF THE PREFERRED EMBODIMENT

In the drawings, reference numeral 1 designates a tubular oxygen detection element formed of a solid electrolyte consisting of zirconia or the like and having a center hole closed at its bottom end 1b. The oxygen detection element 1 is provided with an outer electrode layer 2a extending upwardly from the closed end 1b and composed of a porous thin film formed of platinum or the like and an inner electrode layer 2b extending upwardly from the closed end 1b and composed of a thin film formed of the porous material, the outer and inner electrode layers 2a, 2b being formed by vapor deposition or the like. Reference numeral 3 designates a metal casing composed of a main metal fitting 3' and a metal sleeve 3". The main metal fitting 3' supports the oxygen detection element 1 through its large diameter step seat 1'b and is electrically conductive with the outer electrode layer 2a. The main metal fitting 3' is firmly sealed with the oxygen detection element 1 by means of a sealing material 4 and provided at its lower portion with a thread 3'a adapted to be threadedly engaged with the internal combustion engine wall or the like and with a protection cap 3'b for mechanically protecting the closed end 1b of the oxygen detection element and having small holes 3'c through which the exhaust gas of the internal combustion engine or the like flows into a position near the closed end 1b of the oxygen detection element. The metal sleeve 3" is arranged at the upper end of the sealing material 4 and mechanically and electrically connected to the main metal fitting 3'. The metal sleeve 3" is provided at its upper end with a reduced diameter portion 3"a. Reference numeral 5 designates a center conductor which is provided at its lower end with a coil-shaped terminal 5a threadedly engaged with a threaded open end 1'a of the center bore 1a of the oxygen detection element. As a result, the coil-shaped terminal 5a is electrically conductive with the inner electrode layer 2b formed in the inner peripheral surface of the center bore 1a. The center conductor 5 functions to communicate the atmosphere pressure which is the same as that existed in the outside with the inner electrode layer 2b.

In the present embodiment, the center conductor 5 is provided with a resilient portion 5c such as a coil or the like extending upwardly in the metal sleeve 3" and distant apart from the coil-shaped terminal 5a and operative to apply a tensile force or compressive force to the coil-shaped terminal 5a. A lead wire 5b is interposed between the coil-shaped terminal 5a and the resilient portion 5c. The lead wire 5b may be omitted and the coil-shaped terminal 5a may be made integral with the resilient portion 5c. Reference numeral 6 designates an annular fixing piece formed of insulating material and having an inner diameter surface threadedly engaged, for example, with an upper portion of the resilient portion 5c so as to fix it. The inner diameter surface of the metal sleeve 3" is urged against the outer diameter surface of the annular fixing piece 6 by calking the upper and lower ends 3"c, 3"b of the metal sleeve 3" so as to prevent the resilient portion 5c from displacing in the axial direction thereof. If a spring wire of a harness lead wire to be described later has a high rigidity so that the resilient portion 5c can be held without displacing it in the axial direction thereof, it is possible to omit the fixing piece 6.

The resilient portion 5c of the center conductors 5 is formed such that tensile force or compressive force is applied to the coil-shaped terminal 5a. In practice, if that portion of the resilient portion 5c connected through the lead wire 5b or directly to coil-shaped terminal 5a which is exposed out of the fixing piece 6 has a high rigidity which is sufficient to prevent flexure of the resilient portion 5c, it is preferable to apply tensile force from the resilient portion 5c to the coil-shaped terminal 5a so as to prevent buckling of the latter. In this case, the calked portion 3"c formed at the upper end of the annular fixing piece 6 may be omitted, thereby making the manufacture easy.

Reference numeral 7 designates a harness lead wire used as an output delivering wire and connected to measuring instruments. The harness lead wire 7 is composed of three layers, that is, a spring wire 7a operative as one of the lead wires, an annular resilient insulating material 7b surrounding the spring wire 7a and formed of silicon rubber or the like and a metal mesh 7c surrounding the insulating material 7b and operative as the other lead wire. The lower end of the first spring wire 7a is extended downwardly toward the reduced diameter poriton 3"a and butted against and connected to a tubular terminal 8 of the lead wire 5b of the center conductor 5 by soldering or the like. As a result, the first spring wire 7a becomes electrically conductive with the inner electrode layer 2b of the oxygen detection element. The spring wire 7a is provided therein with a communication hole 7d operative to communicate the outside atmospheric air with the inner electrode layer 2. The third metal mesh 7 is electrically connected by soldering or the like through a metal coupling sleeve 9 and the upper end of the reduced diameter portion 3"a of the outer sleeve 3" to the outer electrode layer 2a of the oxygen detection element.

As stated hereinbefore, the oxygen detector according to the invention is provided at its center conductor with a coil-shaped terminal closely engaged with a thread provided in the open end of an inner electrode layer formed on the inner peripheral wall of a bore of an oxygen detection element and electrically conductive with the inner electrode layer and operative to communicate the bore with the outside atmospheric pressure and with a resilient portion operative to apply tensile force or compressive force to the coil-shaped terminal, and as a result, even when portions near the coil-shaped terminal are exposed to a high temperature, it is possible to maintain the closely threaded engagement between the coil-shaped terminal and the thread provided in the open end of the oxygen detection element and hence ensure an electrical conduction of the inner electrode layer with the center conductor.

What is claimed is:

1. An oxygen detector comprising a tubular oxygen detection element closed at one end and including outer and inner electrode layers extending upwardly from the closed end, the inner electrode layer terminating in a threaded upper end, casing means for sealing the oxygen detection element, said casing means having a metal casing electrically connected with the outer electrode layer of the oxygen detection element, a center conductor disposed within said casing means and including a flexible coil-shaped terminal threadedly engaged with the threaded upper end of said inner electrode layer, an output delivering electric wire assembly fixed to an end of said casing means and having a coil spring lead wire (7a) and an annular resilient insulating material (7b) therearound so as to define a communicating hole (7d) for communicating the inner electrode layer of the oxygen detection element with the outside air, said coil spring lead wire connected electrically to said center conductor, wherein said center conductor has a resilient portion operative to apply a tensile force to the coil-shaped terminal of said center conductor to ensure contact between said coil-shaped terminal and said threaded end of said inner electrode layer, and said resilient portion is firmly fixed to said metal casing with an insulating material (6).

2. The oxygen detector according to claim 1, wherein said resilient portion is composed of a coil and connected through a lead wire to said coil-shaped terminal.

3. The oxygen detector according to claim 1, wherein said resilient portion is made integral with said coil-shaped terminal.

4. The oxygen detector according to claim 1, wherein said center conductor comprises a first lead wire having a first end connected to said coil spring lead wire of said output delivering electric wire assembly and a second end, said resilient portion having a first end fixedly connected with the second end of said first lead wire and a second end, and a second lead wire having a first end fixedly connected with the second end of said resilient portion and a second end connected with said coil-shaped terminal.

5. The oxygen detector according to claim 1, wherein said center conductor is a one-piece member having a first end connected to said coil spring lead wire of said output delivering electric wire assembly and a second end forming said coil-shaped terminal, said resilient portion being intermediate said first and said second ends of said center conductor.

6. The oxygen detector according to claim 1, claim 4, or claim 5, further comprising an annular fixing piece disposed within said casing means and having a threaded bore extending therethrough, and means for fixing the position of said annular fixing piece in said casing means, said resilient portion passing through said threaded bore and having a part thereof threadedly engaged with the annular fixing piece to thereby fix the position of said resilient portion in said casing means.

7. The oxygen detector according to claim 1, wherein said center conductor includes coil-shaped terminals at each end thereof adapted to engage said inner electrode layer and said wire assembly, respectively, a rigid lead wire extending from each of said coil-shaped terminals to a coil-shaped central member, said central member securely received in an insulating annular fixing piece secured to said casing means, a portion of said coil-shaped central member having coils extending beyond said annular fixing piece toward said threaded end of said inner electrode layer to define a resilient portion, said rigid lead wire on opposite sides of said annular fixing piece having an outer diameter less than the inner diameter of said casing means, whereby a continuous open communication path is provided between said inner electrode layer and said wire assembly to permit communication with the atmosphere.

8. An oxygen detector comprising:
 a tubular oxygen detection element closed at one end and including outer and inner electrode layers extending upwardly from the closed end, the inner electrode layer terminating in a threaded upper end,
 casing means for sealing the oxygen detection element, said casing means having a metal casing electrically connected with the outer electrode layer of the oxygen detection element,
 a center conductor disposed within and spaced inwardly of said casing means to permit passage of air between said conductor and said casing, said center conductor including a flexible, coil-shaped terminal threadedly engaged with the threaded upper end of said inner electrode layer, a rigid intermediate portion, and a resilient portion, said resilient portion secured to and extending from an annular fixing piece spaced from said electrode layer and fixed relative to said casing, said annular fixing piece formed from an insulating material and including a communication path to permit air to pass therethrough, and
 an output delivering electric wire assembly having a first component connected to an end of said center conductor and a second component connected to said metal casing, said wire assembly including a communication path for permitting communication of air between said coil-shaped terminal and the inner electrode layer of the oxygen detection element with the outside air, said resilient portion of the center conductor positioned between said coil-shaped terminal and said electric wire assembly and operative to apply a force to the coil-shaped terminal of said center conductor to ensure contact between said coil-shaped terminal and said threaded end of said inner electrode layer under high temperature conditions.

9. The oxygen detector according to claim 8, wherein said center conductor comprises a first lead wire having a first end connected to said output delivering electric wire assembly and a second end, said resilient portion having a first end fixedly connected with the second end of said first lead wire and a second end, and a second lead wire having a first end fixedly connected with the second end of said resilient portion and a second end connected with said coil-shaped terminal.

10. The oxygen detector according to claim 8, wherein said center conductor is a one-piece member having a first end connected to said output delivering electric wire assembly and a second end forming said coil-shaped terminal, said resilient portion being intermediate said first and said second ends of said center conductor.

11. The oxygen detector according to claim 8, further comprising an annular fixing piece disposed within said casing means and having a threaded bore extending therethrough, and means for fixing the position of said annular fixing piece in said casing means, said resilient portion passing through said threaded bore and having a part thereof threadedly engaged with the annular fixing piece to thereby fix the position of said resilient portion in said casing means.

12. The oxygen detector according to claim 9, further comprising an annular fixing piece disposed within said casing means and having a threaded bore extending therethrough, and means for fixing the position of said annular fixing piece in said casing means, said resilient portion passing through said threaded bore and having a part thereof threadedly engaged with the annular fixing piece to thereby fix the position of said resilient portion in said casing means.

13. The oxygen detector according to claim 10, further comprising an annular fixing piece disposed within said casing means and having a threaded bore extending therethrough, and means for fixing the position of said annular fixing piece in said casing means, said resilient portion passing through said threaded bore and having a part thereof threadedly engaged with the annular fixing piece to thereby fix the position of said resilient portion in said casing means.

* * * * *